United States Patent [19]
Stella et al.

[11] Patent Number: 5,985,856
[45] Date of Patent: Nov. 16, 1999

[54] WATER SOLUBLE PRODRUGS OF SECONDARY AND TERTIARY AMINE CONTAINING DRUGS AND METHODS OF MAKING THEREOF

[75] Inventors: Valentino Stella, Lawrence, Kans.; Jeffrey P. Krise, Kersey, Pa.; Jan J. Zygmunt, Longmont, Colo.; Ingrid Gunda Georg, Lawrence, Kans.

[73] Assignee: University of Kansas, Lawrence, Kans.

[21] Appl. No.: 09/222,858

[22] Filed: Dec. 30, 1998

Related U.S. Application Data

[60] Provisional application No. 60/070,093, Dec. 31, 1997.

[51] Int. Cl.$^6$ ....................... A61K 31/675; A61K 31/665; A61K 31/66; C07F 9/6561; C07F 9/6509
[52] U.S. Cl. ............................. 514/80; 514/85; 514/100; 514/114; 540/542; 544/337; 549/220; 558/166; 558/203; 558/131
[58] Field of Search ................................ 514/80, 85, 100, 514/114; 540/542; 544/337; 549/220

[56] References Cited

U.S. PATENT DOCUMENTS

| | | |
|---|---|---|
| 2,947,773 | 8/1960 | Allen ........................................ 558/302 |
| 4,061,722 | 12/1977 | Bodor . |
| 4,160,099 | 7/1979 | Bodor . |
| 4,264,765 | 4/1981 | Bodor et al. . |

FOREIGN PATENT DOCUMENTS

| | | |
|---|---|---|
| 0 279 149 A2 | 8/1988 | European Pat. Off. . |
| 2 173 788 | 10/1986 | United Kingdom . |
| 2 219 584 | 12/1989 | United Kingdom . |
| WO 93/12124 | 6/1993 | WIPO . |
| WO 96/12725 | 5/1996 | WIPO . |

OTHER PUBLICATIONS

Zwierzak, A. et al, Tetrahedron, vol. 27, 1971, pp. 3163–3170 "Organophosphorus Esters–I t–Butyl as Protecting Group in Phosphorylantion."

Bodor, N in Design of Biopharmaceutical Properties through Prodrugs and Analogs, 1977, pp. 98–135, "Novel approaches for the design of membrane . . .".

Bodor, N. et al, J. Med. Chem. 1980, 23, pp. 566–569 "Soft Drugs. 2. Soft alkylating compounds as potential antitumor agents".

Bodor, N., J. Med. Chem. 1980, 23, pp. 474–480 Soft Drugs. 3. A new class of anticholinergic agents.

Bodor, N., Journal of Medicinal Chemistry, vol. 23, No. 5, May 1980, pp. 469–474 "Soft Drugs. 1. Labile quaternary ammonium salts as soft antimicrobilas".

Vinogradova, N.D. et al, Institute of Toxicology(Translated from Khimiko Farmatsevticheskii Zhurnal, vol. 14, No. 9 pp. 41–47, Sep. 1980).

Bogardus, J. et al. Journal of Pharmaceutical Sciences, 729, vol. 71, Jul. 1982, pp. 153–159 "Kinetics and mechanism of hydrolysis of labile . . .".

Bodor, N., ChemTech, Jan. 1984, pp. 28–38 "The soft drug approach".

Varia, S. et al, Journal of Pharmaceutical Sciences, vol. 73, No. 8, Aug. 1984, pp. 1068–1073 "Phenytoin Prodrugs III: Water–soluble prodrugs for . . .".

Varia, S. et al, Journal of Pharmaceutical Sciences, vol. 73, No. 8, Aug. 1984, pp. 1074–1080 "Phenytoin Prodrugs IV: Hydrolysis of various . . .".

Varia, S. et al, Journal of Pharmaceutical Sciences, vol. 73, No. 8, Aug. 1984, pp. 1080–1087 "Phenytoin Prodrugs V: In Vivo evaluation . . .".

Varia, S. et al, Journal of Pharmaceutical Sciences, vol. 73, No. 8, Aug. 1984, pp. 1087–1090 "Phenytoin Prodrugs VI: In Vivo evaluation . . .".

Hammer, R. et al, Bioorganic & Medicinal Chemistry, vol. 1, No. 3, pp. 183–87, 1993 "Soft Drugs XIV: Synthesis and anticholinergic activity . . .".

Tercel, M et al, J. Med. Chem. 1993, 36, pp. 2578–2579 "Nitrobenzyl mustard quaternary salts: A new class of hypoxia–selective . . .".

Davidsen, S. et al, Journal of Medicinal Chemistry, vol. 37, No. 26, Dec. 23, 1994 "N–(Acyloxyalkyl) pyridinium salts as soluble prodrugs . . .".

*Primary Examiner*—Michael G. Ambrose
*Attorney, Agent, or Firm*—Birch, Stewart, Kolasch & Birch, LLP

[57] ABSTRACT

The present invention is drawn to water soluble derivatives aliphatic acid aromatic secondary and tertiary amine containing drugs. The present invention is further drawn to methods of making water soluble derivatives of aliphatic and aromatic secondary and tertiary amine containing drugs.

15 Claims, 3 Drawing Sheets

WATER SOLUBLE PRODRUGS OF SECONDARY AND TERTIARY AMINE CONTAINING DRUGS AND METHODS OF MAKING THEREOF

This application claims priority on provisional application Ser. No. 60/070,093 filed on Dec. 31, 1997, the entire contents of which are hereby incorporated by reference.

FIELD OF THE INVENTION

The present invention is drawn to water soluble derivatives of aliphatic and aromatic secondary and tertiary amine containing drugs. The present invention is further drawn to methods of making water soluble derivatives of aliphatic and aromatic secondary and tertiary amine containing drugs.

BACKGROUND OF THE INVENTION

Many drugs have unfavorable physicochemical properties which create barriers to the attainment of their maximum therapeutic potential. The creation of prodrugs provides a means of chemically modifying drugs in order to temporarily modify the drugs' physicochemical properties. The prodrug is then able to overcome the original barrier, revert back to the parent drug, interact with the receptor and elicit a pharmacological response at the drug's site of action (FIG. 1).

Secondary and tertiary amines often have reasonable aqueous solubility at low pH values but tend to be insoluble around the physiological pH values. Traditional methods for formulating parental dosage forms of tertiary amines have involved non-physiological pH conditions (low pH) and/or exotic, non-aqueous co-solvent addition as well as the use of cyclodextrins and detergents. These traditional methods often have secondary toxicities associated with them which are not observed with the parent drug alone.

Tertiary amines are unusual in chat their derivatization forms quaternary ammonium compounds. However, quaternary salts resulting from simple alkylation of tertiary amines are very stable and do not easily revert back to the parent tertiary amine, thereby limiting their suitability as prodrugs. In addition, if they are used as prodrugs, quaternary ammonium compounds can be quite toxic, therefore the requirement for rapid conversion to the parent tertiary amine is essential. Bodor (U.S. Pat. No. 4,160,099; U.S. Pat. No. 4,254,765; U.S. Pat. No. 4,061,722; Bodot, N. 1981; Bodor, N. et al., 1980(a); Bodor, 1984; Bodor, N. et al., 1980(b)) has developed a class of labile quaternary ammonium salts having a general structure depicted in Formula 1.

(Formula I)

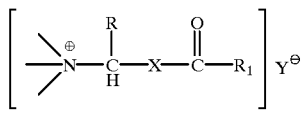

In this structure, R and $R_1$ each represent hydrogen, alkyl, or aryl; X is oxygen or sulfur and Y is a halogen. These compounds hydrolyze to yield the parent tertiary amine, an aldehyde (RCHO), a carboxylic acid ($R_1$COXH), and HY. Applications of this approach have included the preparation of soft quaternary germicides, antiglaucoma agents, anticholinergic agents, and antitumor agents. (Hammer et al., 1993; Bodor, N. and Kaminski, J., 1980; Bodor, N., 1977).

Vinogradova et al. have studied tertiary amine prodrugs using a variety of tertiary amines of various chemical structures representing different pharmacological classes of drugs (Vinogradova, N. et al., 1980). The general structure of the prodrugs of Vinogradova et al. is shown in Formula II where R is alkyl or acyl and X is a halogen.

(Formula II)

Another example of a prodrug of a tertiary amine is that of Bogardus et al. having the labile quaternary salt of Formula III, where R represents H, $CH_3$ or $CH_3CO$. (Bogardus, J. et al., 1982).

(Formula III)

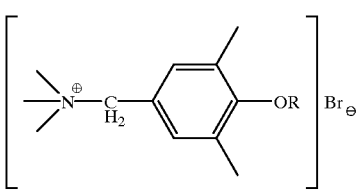

However, the possible production of a quinone methide intermediate following decomposition may preclude this prodrug from clinical application due to toxicity.

Tercel et al. have proposed the tertiary amine prodrug for the nitrogen mustard anti-cancer agent mechlorethamine shown in Formula IV(a) and (b) Formula IV(a) shows the parent drug mechlorethamine and Formula IV(b) shows the proposed hypoxia-selective tertiary amine prodrug. (Tercel, M., et al., 1993).

(Formula IV(a))

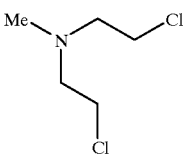

(Formula IV(b))

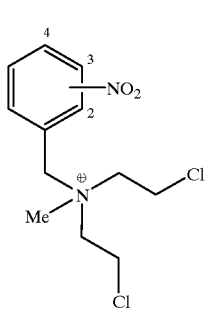

The nitrrobenzyl promoiety of the prodrug of mechlorcethamine was designed primarily as a new class of hypoxia-selective cytotoxin. The quaternary nature of the prodrug deactivates the mustard and increases its water solubility. One electron reduction of the nitroaromatic portion causes the release of the reactive aliphatic mustard in cells which are deprived of oxygen, such as those in solid tumors.

Davidson investigated the ability of N-(acyloxyalkyl) pyridinium salts to enhance the solubility of a platelet activating factor antagonist (Davidson, S., et al., 1994). The general structure of these prodrugs is shown in Formula V, where buffer and plasma stability can be adjusted through variations of $R_1$ and $R_2$.

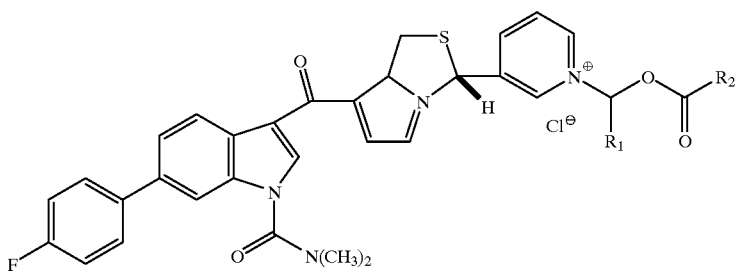

(Formula V)

The use of a methylene-spaced phosphate group applied to an imide and an alcohol has been reported as a promoiety in two separate reports. Varia and Stella were the first to report on the use of this prodrug strategy when they described a water-soluble phenytion prodrug, 3-(hydroxymethyl)-5,5-diphenylhydantion disodium phosphate ester (Varia, S., et al., 1984(a); Varia, S. et al., 1984(b); Varia, S. et al., 984(c); Varia, S. et al., 1984(d)). This prodrug was shown to be a substrate for alkaline phosphatase, an enzyme ubiquitous to the human body. The prodrug breaks down in the presence of alkaline phosphatase to give the parent drug, formaldehyde, and inorganic phosphate as shown in Reaction Scheme I.

Reaction Scheme I

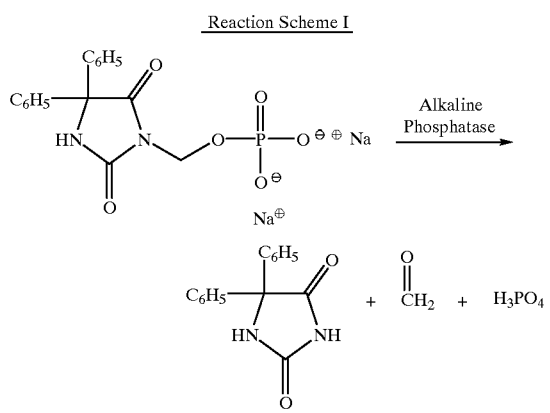

The second use of the promoiety was presented in EP 0 604,910 A1 by Golik et al. The investigators described prodrugs with derivatization on the 2'- and 7-position alcohols of the taxane molecule. The prodrugs were created in an effort to improve the poor aqueous solubility of taxol. This prodrug also degraded in the presence of alkaline phosphatase to give the parent taxane derivative, formaldehyde and inorganic phosphate. However, neither Varia and Stella nor Golik et al. apply this technology to amine drugs.

SUMMARY OF THE INVENTION

The present invention is drawn to N-phosphoryloxymethyl prodrugs of secondary and tertiary amine containing drugs having the following formula VI,

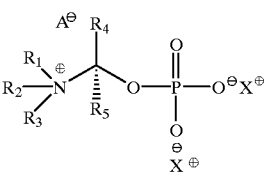

(Formula VI)

wherein $R_1$, $R_2$ and $R_3$ are substituents which comprise the parent secondary or tertiary amine such that one of $R_1$, $R_2$ or $R_3$ may be hydrogen, $R_4$ and $R_5$ are each hydrogen, or an organic or inorganic residue.

Examples of $R_4$ and $R_5$ include but are not limited to:

i) straight chain aliphatic groups such as $-CH_3$, $-CH_2CH_3$, etc.

ii) any aromatic or cyclic substituent such as phenyl, benzyl, cyclohexane, etc.

iii) any combination of i) and ii) with or without additional functional groups and/or heteroatoms.

The substituents on $R_4$ and $R_5$ may be the same or different. The two substituents may be joined through a chemical bond to form a complete ring to give Formula VIa:

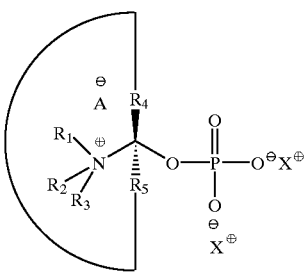

(Formula VIa)

The carbon spacer may alternatively be double bonded to a moiety represented by $R_6$. The substituent $R_6$ may be any of examples i), ii) or iii) above. The structure of this is shown in formula VIb.

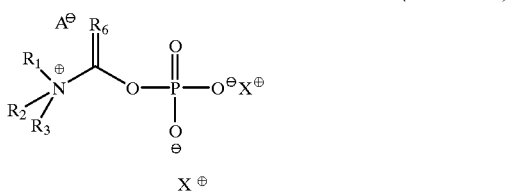

(Formula VIb)

X is a pharmaceutically acceptable cationic organic or inorganic salt.

Formulae VI, VIa, and VIb all have an external anion (A) associated with the quaternary amine center and an external cation (X) associated with the phosphate dual anionic charge. Also contemplated by the present invention are those compounds where the quanternary ammonium center's cationic charge is internally balanced with one of the anionic charges generated from the phosphate. The ability of the prodrugs to take the form of the internal salt may be dependent upon the structure and charge of the parent tertiary amine. A representation of this issue is shown below. Structure 1 may exist at very low pH (pH<pKa1). In this pH range only structure 1 could exist (e.g., no other salt form). The first pKa for this phosphate monoester is assumed to be around 1. Structures 2 and 3 are the possible salt forms at pH near 3. Structures 4 and 5 would be the possible salt forms at physiological pH and higher. Although the formulae of the present specification are shown in the external salt form, the present invention also encompasses the internal salt form.

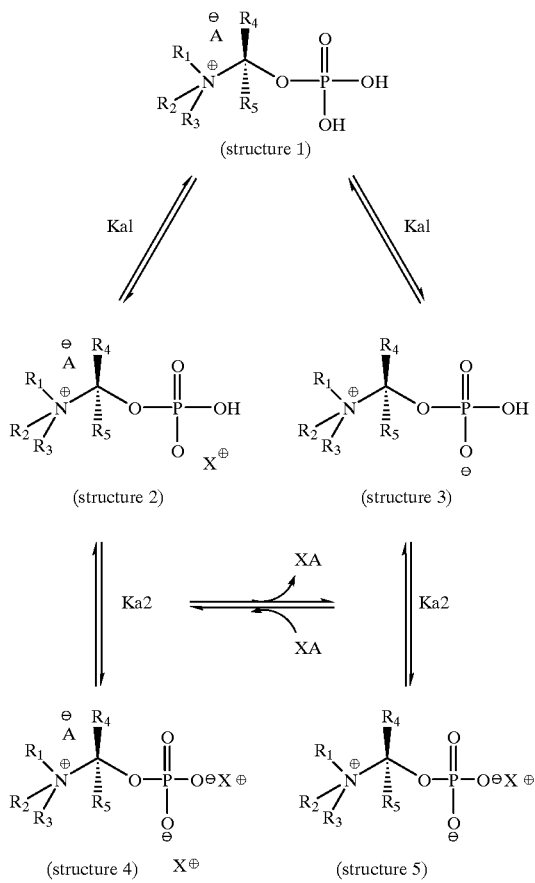

The present invention is further drawn to pharmaceutical compositions containing N-phosphoryloxymethyl prodrugs of secondary or tertiary amine containing drugs.

Another object of the present invention is to provide N-phosphoryloxymethyl prodrugs of secondary or tertiary amine containing drugs which are soluble in aqueous pharmaceutical carriers and which have reduced toxic side effects.

The present invention is further drawn to a first method of making a soluble prodrug of a secondary and tertiary amine containing parent drug comprising derivatization of a pro drug moiety of formula VII

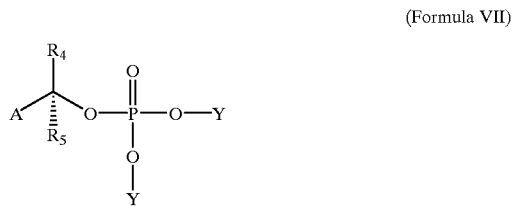

(Formula VII)

wherein A represents a leaving group, $R_4$ and $R_5$ are each an organic or inorganic residue as described above, and Y is a phosphate protecting group. A prodrug of the present invention is formed through the nucleophilic attack by a tertiary amine causing the displacement of A, followed by the removal of the protecting groups.

Also within the scope of the present invention is a second method of making a soluble prodrug of a tertiary amine containing parent drug comprising reaction of a compound of the following Formula VIII

(Formula VIII)

wherein $R_4$ and $R_5$ are each an organic or inorganic residue as described above, and W and Z are leaving groups, with a tertiary amine to displace one of either W or Z and reacting the remaining leaving group with a protected phosphate salt.

DETAILED DESCRIPTION OF THE INVENTION

Figure 1:
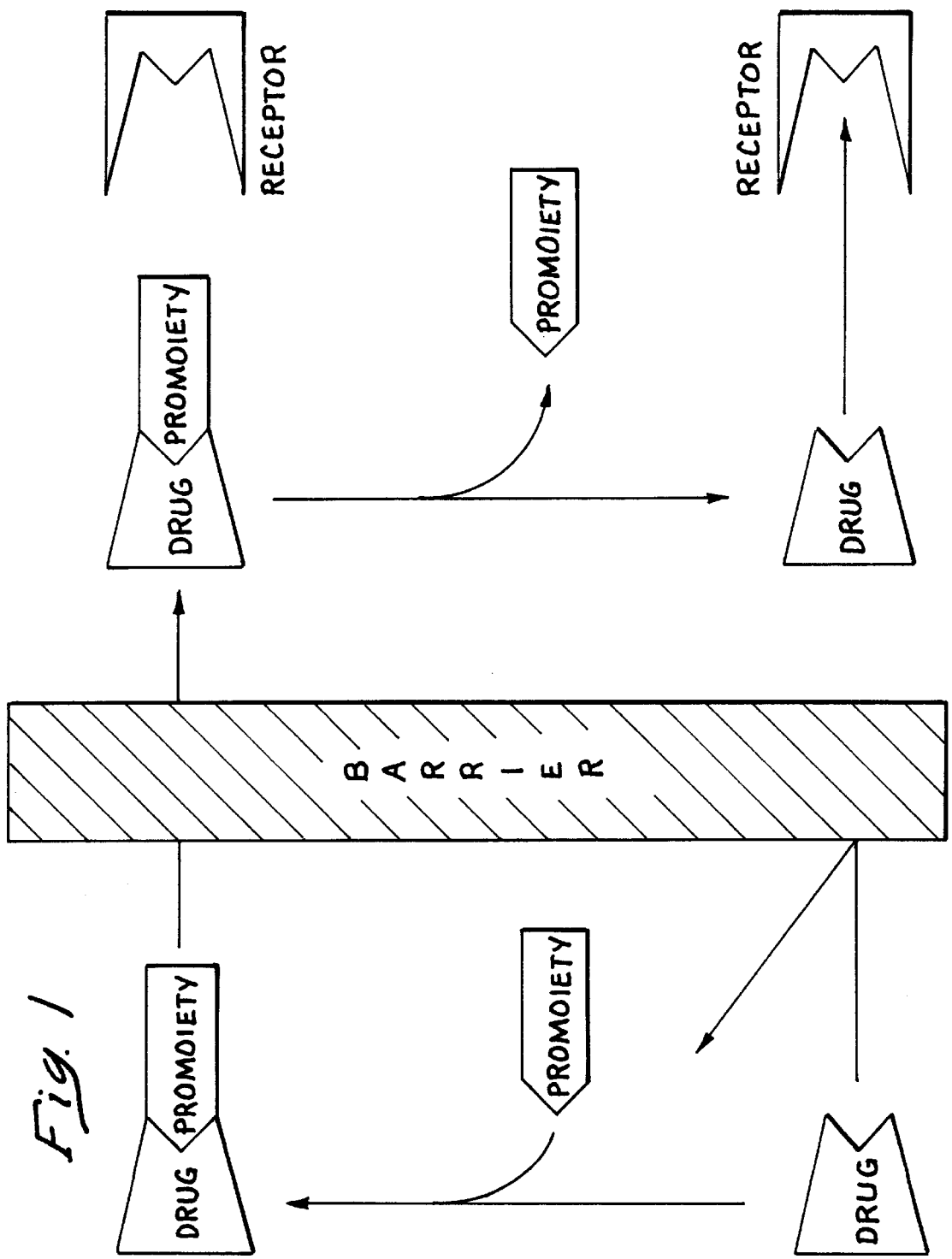
FIG. 1 shows the graphic representation of a prodrug model.

The present invention is drawn to prodrugs of secondary and tertiary amines formed through a bioreversible derivatization to yield prodrugs with improved aqueous solubility and good chemical stability in the physiological pH range without the need for co-solvent addition. The general prodrug structure of the present compounds is shown in Formula VI.

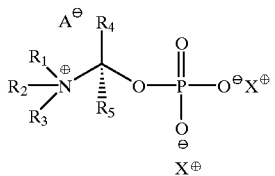

(Formula VI)

Formula VI shows the general structure of the present N-phosphoryloxymethyl prodrugs of secondary and tertiary amine containing drugs, wherein $R_1$, $R_2$, and $R_3$ are substituents which comprise the parent secondary or tertiary amine such that one of $R_1$, $R_2$ or $R_3$ may be hydrogen. The remainder of the structure is the promoiety. $R_4$ and $R_5$ can each be any organic or inorganic residue.

Examples of $R_4$ and $R_5$ include but are not limited to:
i) straight chain aliphatic groups such as —$CH_3$, —$CH_2CH_3$, etc.
ii) any aromatic or cyclic substituent such as phenyl, benzyl, cyclohexane, etc.
iii) any combination of i) and ii) with or without additional functional groups and/or heteroatoms.

The substituents on $R_4$ and $R_5$ may be the same or different. The two substituents may be joined through a chemical bond to form a complete ring to give Formula VIa:

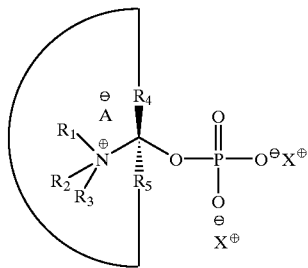

(Formula VIa)

The carbon spacer may alternatively be double bonded to a moiety represented by $R_6$. The substituent $R_6$ may be any of examples i), ii) or iii) above. The structure of this is shown in formula VIb.

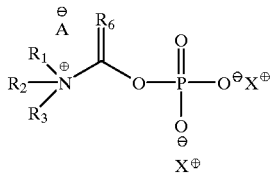

(Formula VIb)

X can be any pharmaceutically acceptable cationic organic or inorganic salt.

Formulae VI, VIa, and VIb all have an external anion (A) associated with the quaternary amine center and an external cation (X) associated with the phosphate dual anionic charge. Also contemplated by the present invention are those compounds where the quanternary ammonium center's cationic charge is internally balanced with one of the anionic charges generated from the phosphate. The ability of the prodrugs to take the form of the internal salt may be dependent upon the structure and charge of the parent tertiary amine. A representation of this issue is shown below. Structure 1 may exist at very low pH (pH<pKa1). In this pH range only structure 1 could exist (e.g., no other salt form). The first pKa for this phosphate monoester is assumed to be around 1. Structures 2 and 3 are the possible salt forms at pH near 3. Structures 4 and 5 would be the possible salt forms at physiological pH and higher. Although the formulae of the present specification are shown in the external salt form, the present invention also encompasses the internal salt form.

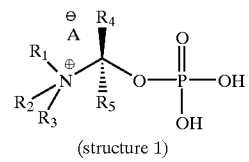

(structure 1)

Ka1     Ka1

(structure 2)     (structure 3)

Ka2    XA    Ka2

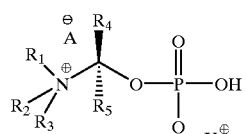

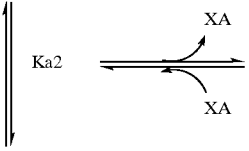 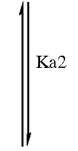

(structure 4)   X⊕     (structure 5)

The non-obviousness of the present prodrug is two fold. The first non-obvious characteristic of the derivative is the ionic nature. As stated earlier, molecules containing quaternary ammonium centers, in general, can be quite toxic. But with the compounds of the present invention, the attached promoiety can have up to two negative charges (depending on the pH of the environment), one of which can serve to mask the positively charged quaternary center contained in the prodrug molecule. This is believed to reduce the potential toxicity since the body will no longer recognize and treat the prodrug as a quaternary ammonium compound. Secondly, no one has described an alkyl phosphate derivative of a secondary or tertiary amine to produce the quaternary ammonium prodrug. Although it has been common practice for researchers to make reversible chemical modifications on functional groups such as alcohols, carboxylic acids, and primary and secondary amines, it is often the case that either these functional groups are not present in the molecule or the chemical modification of these groups is difficult. The tertiary amine group has received little if any attention (except for those mentioned earlier) as a derivatizable functional group, which is surprising considering the fact that tertiary amine-containing drugs are a vast and important category of drugs.

Suitable pharmaceutical carriers for the present invention include any aqueous carriers which are useful for administering the drug or prodrug, preferably those which are non-toxic, otherwise inert, medically acceptable and compatible with the prodrug. Particularly useful are buffer saline based carriers. The present compositions may further comprise other active ingredients such as antimicrobial agents and other agents such as preservatives.

The present compositions are typically prepared for injectable formulations but are not limited to parenteral formulations. The present composition may also be used in extravascular formulations such as oral, intramuscular and subcutaneous administerable forms. The pharmaceutically active agent or prodrug will typically be present in a concentration of 0.1–1000 mg/ml preferably, 1–100 mg/ml, more preferably 2–50 mg/ml. The present compositions are further formulated in a physiologically acceptable pH range. The pH of the present compositions is between 4.5–9.5, preferably between 6.5–8.5, more preferably between 7.4–8.0. The present invention is further drawn to lyophilized forms of the prodrug which may contain a suitable buffer reagent. The prodrug may be lyophilized in single dosage vials such that an appropriate single dose is achieved upon reconstitution in a suitable buffer or water.

The present prodrug may also be in a solid form. The solid form may be as a tablet, dry powder or granules. The solid form may also contain a suitable binder material or coating agent.

The present invention is further drawn to methods of making tertiary amine prodrugs. One method for the synthesis of prodrugs involves a derivatizing reagent of the general form represented in Formula VII.

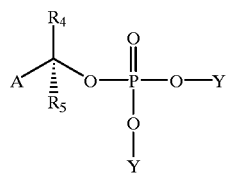

(Formula VII)

With Formula VII, A represents any leaving group. A leaving group, as is depicted in formula VII, is a group that is displaced by a nucleophilic tertiary amine group in a bimolecular combination reaction. The rate of the reaction is sensitive to, among many other factors, the leaving ability of the group being displaced. The leaving group can be of several types. Examples of suitable leaving groups include but are not limited to tosylate, triflate, iodine, bromine, chlorine, fluorine, acetate, hydroxyl, etc. Further discussion of suitable leaving groups and examples thereof can be found in Hatshorn, S. R., *Aliphatic Nucleophilic Substitution*. Cambridge (Eng.), University Pres, 1973.

$R_4$ and $R_5$ represent any organic or inorganic residue.

Y represents a phosphate protecting group. A phosphate protecting group is a group that is used to temporarily block the reactive phosphate moiety in order for the described nucleophilic displacement reaction to be carried cut selectively. The phosphate protecting group must be able to be selectively removed after the reaction is completed. Examples of phosphate protecting groups contain but are not limited to tertiary butyl, benzyl, isopropyl, ethyl, β-cyanoethyl etc. Further discussion of appropriate phosphate protecting groups may be found in McOmie, J. F. W., *Protective Groups in Organic Chemistry*. London and New York, Plenum Press, 1973 and Green, T. W., Wuts, G. M., *Protective Groups in Organic Synthesis*, 2nd Edition, New York, Wiley, 1991.

The prodrug synthesis as depicted in Reaction Scheme II involves nucleophilic attack by the tertiary amine causing the displacement of A. The protecting groups are then removed to give the prodrug.

(Reaction Scheme II)

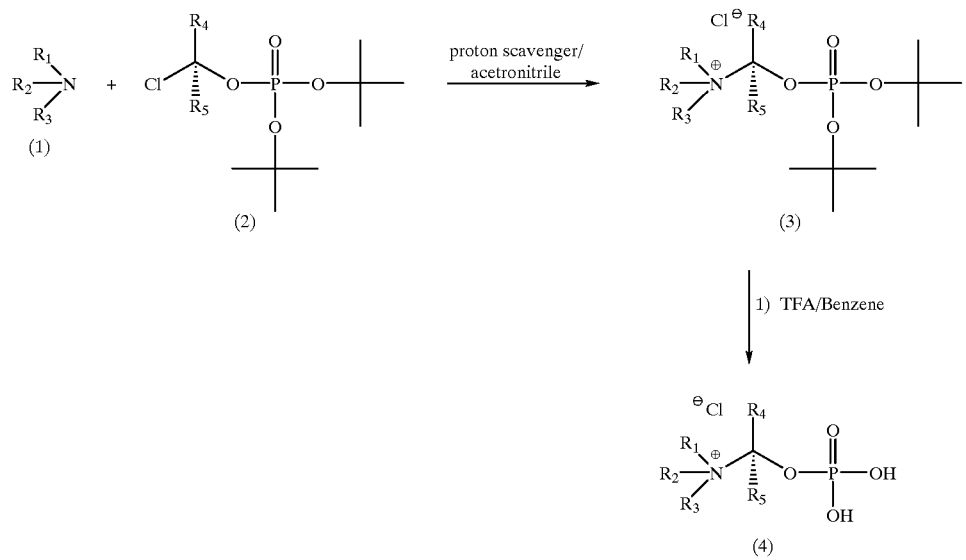

A second proposed method for the synthesis of the prodrugs is represented in Reaction Scheme III.

(Reaction Scheme III)

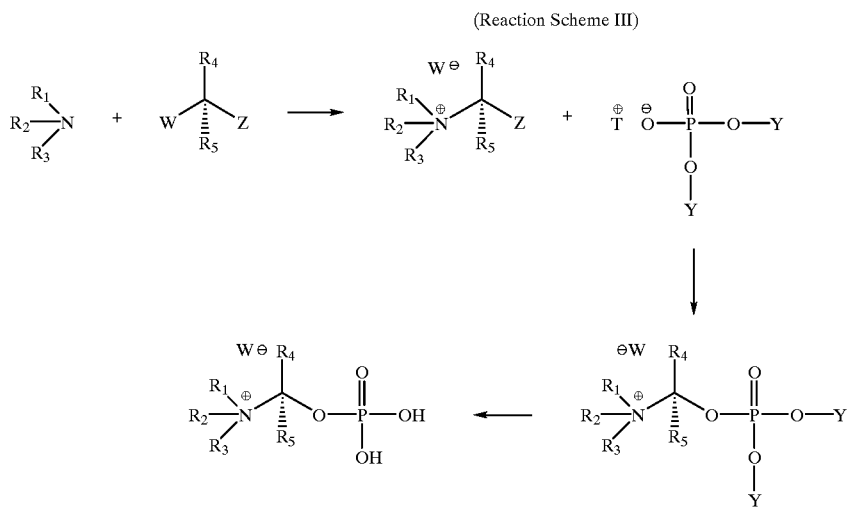

In Reaction Scheme III, $R_1$, $R_2$, and $R_3$ are the substituents which comprise the parent tertiary or secondary amine. $R_4$ and $R_5$ can be any organic or inorganic residue as described above. W and Z are leaving groups; they can be the same or they could vary in their reactivity. The leaving groups W and Z are each a group that is displaced by a nucleophilic tertiary amine group in a bimolecular combination reaction. The rate of the reaction is sensitive to, among many other factors, the leaving ability of the group being displaced. The leaving group can be of several types. Examples of suitable leaving groups include but are not limited to tosylate, trifilate, iodine, bromine, chlorine, fluorine, acetate, hydroxyl, etc. Further discussion of suitable leaving groups and examples thereof can be found in Hatshorn, S. R., *Aliphatic Nucleophilic Substitution*. Cambridge (Eng.), University Pres, 1973. T is any organic or inorganic cationic specie. Y is, as above, any phosphate protecting group. This method involves a two step procedure to obtain the protected prodrug. The parent tertiary amine is reacted with the reagent under conditions where only one leaving group (W or Z) is displaced. The second step of the reaction involves displacement of the second leaving group (Z in the above scheme) by the protected phosphate salt. The prodrug is then deprotected.

Tertiary and secondary amine drugs which are contemplated as being useful in the present invention and which may be converted to prodrugs using the present methods include the following.

1) Aliphatic secondary and tertiary alkyl amines.

These types of amines have two or three organic substituents attached to the nitrogen atom, respectively. The representative structure is shown in Formula IX.

(Formula IX)

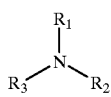

$R_1$, $R_2$, and $R_3$ each represent an organic substituent or one of $R_1$, $R_2$ or $R_3$ may represent a hydrogen. The organic substituents can be of aliphatic nature resulting in an alkyl substituted tertiary amine. If any or all of the organic substituents, $R_1$, $R_2$ and $R_3$, are aromatic, then this amine is referred to as an aryl substituted tertiary or secondary amine. Examples of pharmaceutical compounds with this classification are as follows:

amiodarone, amitryptyline, azithromycin, benzphetamine, bromopheniramine, cabinoxamine, chlorambucil, chloroprocaine, chloroquine, chlorpheniramine, chlorpromazine, cinnarizine, clarthromycin, clomiphene, cyclobenzaprine, cyclopentolate, cyclophosphamide, dacarbazine, demeclocycline, dibucaine, dicyclomine, diethylproprion, diltiazem, dimenhydrinate, diphenhydramine, disopyramide, doxepin, doxycycline, doxylamine, dypyridame, EDTA, erythromycin, flurazepam, gentian violet, hydroxychloroquine, imipramine, levomethadyl, lidocaine, loxarine, mechlorethamine, melphalan, methadone, methotimeperazine, methotrexate, metoclopramide, minocycline, naftifine, nicardipine, nizatidine, orphenadrine, oxybutin, oxytetracycline, phenoxybenzamine, phentolamine, procainamide, procaine, promazine, promethazine, proparacaine, propoxycaine, propoxyphene, ranitidine, tamoxifen, terbinafine, tetracaine, tetracycline, tranadol, triflupromazine, trimeprazine, trimethylbenzamide, trimipramine, trlpelennamine, troleandomycin, uracil mustard, and verapamil.

2) Nitrogen-containing heterocycles.

These types of amines can be categorized as either aromatic or non-aromatic. There can be three types of non-aromatic heterocycles. One type contains a $sp^2$ hybridized nitrogen and the other two types have a $sp^3$ hybridized nitrogen. The two $Sp^3$ hybridized heterocycles are represented in Formula X.

(Formula X)

structure A structure B

In Formula X, the represented rings can be constructed solely from carbon atoms or can contain atoms other than carbon; $R_1$ can be any organic substituent (structure A) or this substituent may be a part of a separate but adjoining ring (structure B). Examples of pharmaceutical compounds of this type are as follows:

acravistine, amoxapine, astemizole, atropine, azithromycin, benzapril, benztropine, beperiden, bupracaine, buprenorphine, buspirone, butorphanol, caffeine, ceftriaxone, chlorpromazine, ciprofloxacin, cladarabine, clemastine, clindamycin, clofazamine, clozapine, cocaine, codeine, cyproheptadine, desipramine, dihydroergotamine, diphenidol, diphenoxylate, dipyridamole, doxapram, ergotamine, famciclovir, fentanyl, flavoxate, fludarabine, fluphenazine, fluvastin, ganciclovir, granisteron, guanethidine, haloperidol, homatropine, hydrocodone, hydromorphone, hydroxyzine, hyoscyamine, imipramine, itraconazole, keterolac, ketoconazole, levocarbustine, levorphone, lincomycin, lomefloxacin, loperamide, losartan, loxapine, mazindol, meclizine, meperidine, mepivacaine, mesoridazine, methdilazine, methenamine, methimazole, methotrimeperazine, methysergide, metronidazole, minoxidil, mitomycin c, molindone, morphine, nafzodone, nalbuphine, naldixic acid, nalmefene, naloxone, naltrexone, naphazoline, nedocromil, nicotine, norfloxacin, ofloxacin, ondansteron, oxycodone, oxymorphone, pentazocine, pentoxyfylline, perphenazine, physostigmine, pilocarpine, pimozide, pramoxine, prazosin, prochlorperazine, promazine, promethazine, quinidine, quinine, rauwolfia alkaloids, riboflavin, rifabutin, risperidone, rocuronium, scopalamine, sufentanil, tacrine, terazosin, terconazole, terfenadine, thiordazine, thiothixene, ticlodipine, timolol, tolazamide, tolmetin, trazodone, triethylperazine, trifluopromazine, trihexylphenidyl, trimeprazine, trimipramine, tubocurarine, vecuronium, vidarabine, vinblastine, vincristine and vinorelbine.

Alternatively, the heterocycle may be bonded to one adjacent atom through a double bond in which case the nitrogen becomes $sp^2$ hybridized. These heterocycles can be either aromatic or non-aromatic. This type of heterocycle is shown in Formula XI.

(Formula XI)

Examples of pharmaceutical compounds falling under the aromatic classification are as follows:

acetazolamide, acravistine, acyclovir, adenosine phosphate, allopurinal, alprazolam, amoxapine, amrinone, apraclonidine, azatadine, aztreonam, bisacodyl, bleomycin, bromopheniramine, buspirone, butoconazole, carbinoxamine, cefamandole, cefazole, cefixime, cefmetazole, cefonicid, cefoperazone, cefotaxime, cefotetan, cefpodoxime, ceftriaxone, cephapirin, chloroquine, chlorpheniramine, cimetidine, cladarabine, clotrimazole, cloxacillin, didanosine, dipyridamole, doxazosin, doxylamine, econazole, enoxacin, estazolam, ethionamide, famciclovir, famotidine, fluconazole, fludarabine, folic acid, ganciclovir, hydroxychloroquine, iodoquinol, isoniazid, itraconazole, ketoconazole, lamotrigine, lansoprazole, lorcetadine, losartan, mebendazole, mercaptopurine, methotrexate, metronidazole, miconazole, midazolam, minoxidil, nafzodone, naldixic acid, niacin, nicotine, nizatidine, omeperazole, oxaprozin, oxiconazole, papaverine, pentostatin, phenazopyridine, pilocarpine, piroxicam, prazosin, primaquine, pyrazinamide, pyrimethamine, pyroxidine, quinidine, quinine, ribaverin, rifampin, sulfadiazine, sulfamethizole, sulfamethoxazole, sulfasalazine, sulfasoxazole, terazosin, thiabendazole, thiamine, thioguanine, timolol, trazodone, triampterene, triazolam, trimethadione, trimethoprim, trimetrexate, triplenamine, tropicamide, vidarabine Examples of pharmaceuticals containing the non-aromatic or cyclic imine functional group are as follows:

allopurinal, alprazolam, astemizole, caffeine, capriomycin, chlorazepate, chlordiazepoxide, chlorthiazide, clonazepam, clozapine, dacarbazine, dactinomycin, diazoxide, estazolam, famciclovir flurazepam, folic acid, granisteron, halazepam, lorazepam, loxapine, mazindol, midazolam, ondansteron, oxazepam, oxymetazoline, pemoline, pentostatin, pentoxyfylline, phentolamine, quazepam, riboflavin, rifabutin, risperidone, temazepam, tetrahydrazoline, tolazoline, triazolam, vidarabine, xylometazoline 3) Azo compounds.

These compounds have the general structure shown in Formula XII.

$$R_1-N=N-R_2 \qquad \text{(Formula XII)}$$

Figure 4:
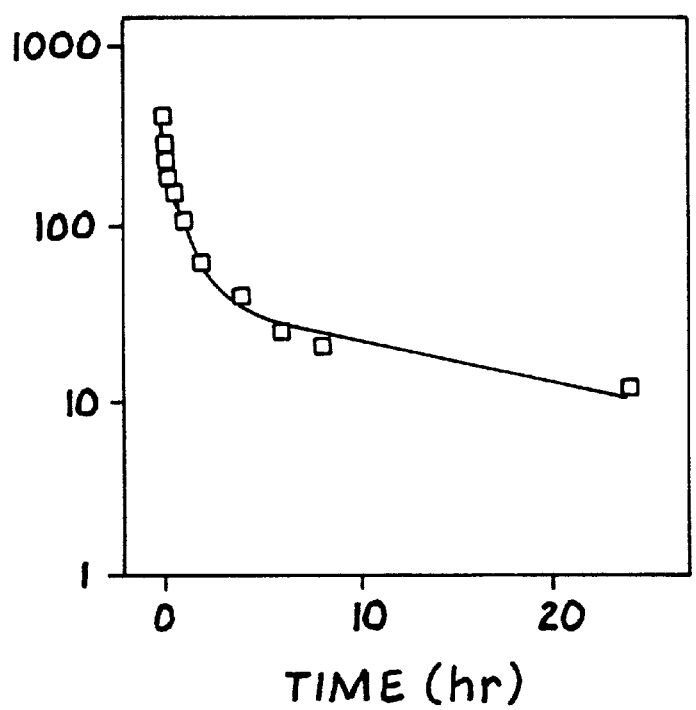
FIG. 4 shows the semilogarithmic plot of cinnarizine concentration in plasma versus time after i.v. injection of 33.9 nmole of cinnarizine to the beagle dog.

In FIG. 4, $R_1$ and $R_2$ can represent any organic substituents. Examples of pharmaceutical compounds of this type are phenazopyridine and sulfasalazine.

4) Imine containing drugs.

This classification of amine is represented in Formula XIII.

(Formula XIII)

$$R_1 \atop R_2 \Big\rangle C=N-R_3$$

In Formula XIII, $R_1$ and $R_2$ can represent hydrogen or any type of organic substituent in any combination. $R_3$ can represent any type of organic substituent. In the case where $R_1$ and $R_2$ are organic substituents, they can be separate groups or can be combined to represent a ring. Examples of pharmaceutical compounds falling under this classification are as follows:

cefixime, cimetidine, clofazimine, clonidine, dantrolene, famotidine, furazolidone, nitrofurantoin, nitrofurazone, oxiconazole.

EXAMPLES

The mechanism (shown above in Reaction Scheme II) for the creation of prodrugs involves a nucleophilic attack by the parent tertiary amine (1) on the methylene group of chloromethyl di-tert-butyl phosphate (2) via an $SN_2$ type displacement of the halogen leaving group. The first step of this reaction is carried out in the presence of a large excess of a proton scavenger, 1,2,2,6,6 pentamethyl piperidine. The proton scavenger is principally used to capture HCl—a product from the breakdown of (2) and/or (3).

The tertiary butyl-protected prodrug (3) is then purified using preparative thin layer chromatography or preparative HPLC. The tertiary butyl-protecting groups are then removed with triflouroacetic acid in benzene at room temperature to yield the free acid which can be readily converted to a desired salt form (4).

The prodrug synthesis is exemplified below with the following four chemical entities, each containing one or more tertiary amine groups.

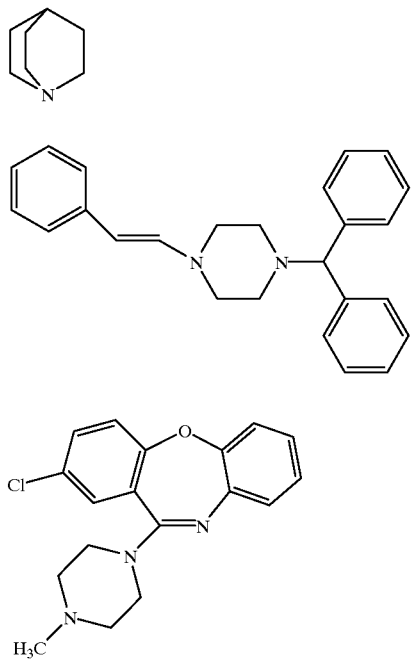

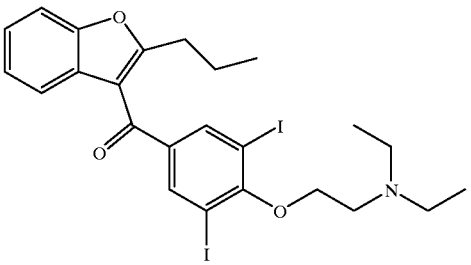

Quinuclidine (5) is a highly reactive tertiary amine which is not pharmacologically active and is used as a model compound. The other three molecules are drugs. Cinnarizine (6) is an antihistaminic drug, loxapine (7) is an antipsychotic agent, and amiodarone (8) is a cardiotonic agent. The latter three molecules exhibit very poor aqueous solubility at physiological pH values. Cinnarizine is not currently formulated as an injectable; however, amidarone hydrochloride is available as an intravenous injection and loxapine hydrochloride is available as an intramuscular injection. Both amidarone hydrochloride and loxapine hydrochloride are formulated at a concentration of 50 mg/ml with the help of cosolvents and a lowered pH.

Example 1

Synthesis of chloromethyl di-tert-butyl phosphate (Reaction Scheme IV)

Materials

Di-tert-butyl phosphite is obtained from Lancaster (Windham, N.H.). Potassium bicarbonate ($KHCO_3$) is obtained from Fischer Scientific (Pittsburgh, Pa.).

(Reaction Scheme IV)

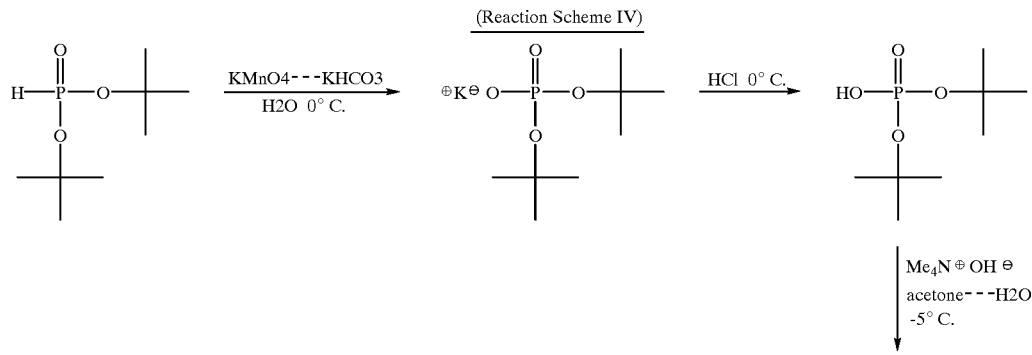

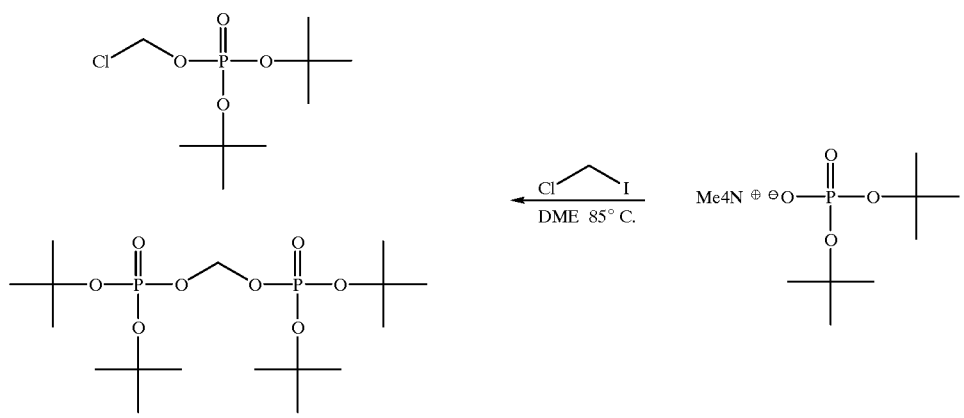

Potassium permanganate (KMnO₄) is obtained from Malinckrodt Chemical Works (St. Louis, Mo.) and is finely powdered prior to use. Tetramethylammonium hydroxide ((CH₃)₄NOH) 10 wt % solution in water is obtained from Aldrich Chemical Company (Milwaukee, Wis.). Chloroiodomethane is obtained from Aldrich Chemical Company, (Milwaukee, Wis.). Normal phase silica gel, particle size 32–63 μM, is obtained from Selecto Scientific (Norcross, Ga.). Anhydrous acetonitrile and dimethoxyethane are also obtained from Aldrich Chemical Company (Milwaukee, Wis.). All water is distilled in an all-glass still prior to use. All other chemicals and solvents are of reagent grade and used without further purification.

Methods

The conversion of di-tert-butyl phosphite into the corresponding phosphate is performed by a slight modification of the method published by Zwierzak and Kluba (Zwierzak, A and Kluba, M., 1971). Di-tert-butyl phospohite (40.36 mmole) is combined with potassium bicarbonate (24.22 mmole) in 35 ml of water. The solution is stirred in an ice bath and potassium permanganate (28.25 mmole) is added in three equal portions over one hour's time. The reaction as then allowed to continue at room temperature for an additional half hour. Decolorizing carbon (600 mg) is then incorporated as the reaction is heated to 60° C. for 15 minutes. The reaction is then vacuum filtered to remove solid magnesium dioxide. The solid is washed several times with water. The filtrate is then combined with one gram of decolorizing carbon and heated at 60° C. for an additional twenty minutes. The solution is again filtered to yield a colorless solution, to which a slight excess of concentrated HCl is slowly added with efficient stirring in an ice bath. The addition of acid causes the precipitation of the di-tert-butyl phosphate free acid. The free acid is then filtered and washed with ice cold water. The compound is then converted to the salt form by dissolving the free acid in acetone and adding an equal molar amount of tetramethylammonium hydroxide while keeping the reaction cooled by a salt/ice bath with efficient stirring. The resulting clear solution is placed under reduced pressure to give 7.16 grams of crude product. This product is then recrystallized by refluxing in dimethoxyethane and slow cooling at room temperature to give 6.52 g of pure product (57% yield). 12.75 mmole of the tetramethylammonium di-tert-butyl-phosphate is then mixed with 70 ml of dimethoxyethane and brought to reflux. Twenty-five grams of chloroiodomethane is then added and stirred for one and a half hours. The reaction is then filtered and the filtrate is placed under reduced pressure to remove excess chloroiodomethane and solvent. The two products are then separated via flash column chromatography. The stationary phase is normal phase silica (30 g). The mobile phase consists of ethyl acetate and hexane in a 3 to 7 (v/v) ratio respectively. The chloromethyl di-tert-butyl phosphate is isolated as a pale gold oil (63% yield): $^1$H NMR (CDCl₃, 300 MHz) δ 1.51 (s, 12H), 5.63 (d, 2H, J=14.8). Mass spectrum (FAB+, GLY) 259 (M+1).

Example 2

Reaction of chloromethyl di-tert-butyl phosphate with tertiary amines (1) Synthesis of quinuclidine prodrug Materials Quinuclidine is obtained from Aldrich Chemical Company (Milwaukee, Wis.). Chloromethyl di-tert-butyl phosphate is synthesized as previously described. Triflouroacetic acid is obtained from Aldrich Chemical Company (Milwaukee, Wis.).

Methods Quinuclidine (0.64 mmole) is dissolved in 5 ml of anhydrous acetonitrile. An equal molar amount of chloromethyl di-tert-butyl phosphate is added and the reaction is stirred at 37° C. for 12 hours. The reaction is then placed under reduced pressure to remove the solvent at which time 5 ml of anhydrous ethyl ether is added to precipitate the polar product. This suspension is then centrifuged and the supernatant is removed. This process is repeated three times. The solid is then collected and dried to yield 0.487 mmole of protected prodrug (MW 369.6, 78% yield). $^1$H NMR (CDCl₃, 300 MHz) δ 1.54 (s, 18H), 2.07 (m, 6H), 2.27 (m, 1H), 3.86 (t, 6H, J=7.9), 5.36 (d, 2H, J=8.4). $^{31}$P NMR (CDCl₃, 500 MHz) δ −14.9704 (t, J=19.5). Mass spectrum (FAB+, GLY) 334 (M+). Melting point 88–105° C.

The tertiary butyl groups are then removed by addition of 0.38 mmole of triflouroacetic acid in benzene at room temperature for 24 hours. The reaction is then placed under reduced pressure to remove TFA and benzene to yield 0.202 mmole of a white solid: $^1$H NMR (D₂O, 300 Mhz) δ 1.97 (m, 6H), 2.18 (m, 1H), 3.407 (t, 6H, J=7.9), 4.48 (d, 2H, J=6.8). Mass spectrum (FAB+, GLY) 222 (M+).

(2) Synthesis of cinnarizine prodrug

Materials

Cinnarizine is obtained from Sigma Chemical Company (St. Louis, Mo.) 1,2,2,6,6 pentamethylpiperidine is obtained from Aldrich Chemical Company (Milwaukee, Wis.).

Methods

Cinnarizine (0.616 mmole) is combined with a 120 mole percent excess of both chloromethyl di-tert-butyl phosphate and 1,2,2,6,6 pentamethylpiperidine. The reaction components are solubilized in anhydrous acetonitrile. The reaction is allowed to progress at 70° C. for 6 days. The reaction is then placed under reduced pressure to remove the solvent after which time 5 ml of anhydrous ethyl ether is added to precipitate the product. This suspension is then centrifuged and the supernatant is removed. This process is repeated three times. The product is then purified using preparative thin layer chromatography. The eluent is methylene chloride and methanol in a ratio 75 to 25 respectively which gives a Rf of 0.7. The mono tertiary butyl protected prodrug is isolated as a white solid (0.058 mmole, 8% yield): $^1$H NMR (acetonitrile-d3, 300 MHz) δ 1.35 (s, 9H), 2.70 (m, 4H), 3.39 (m, 2H), 3.56 (m, 2H), 4.12 (d, 2H, J=7.8), 4.46 (s, 1H), 5.01 (d, 2H, J=8.43), 6.4 (m, 1H), 6.95 (d, 1H, J=15.76), 7.3 (m, 15H). Mass spectrum (FAB+, GLY) 535 (M+).

The protected prodrug (0.0048 mmole) is incorporated with 0.02 mmole of triflouroacetic acid in benzene at room temperature for 24 hours to remove the tertiary butyl protecting groups. The reaction is then placed under reduced pressure to remove TFA and benzene to yield 0.042 mmole (87% yield) of a white solid: $^1$H NMR (D$_2$O, 300 Mhz) δ 2.98 (m, 4H), 3.58 (m, 4H), 4.23 (d, 2H, J=7.77), 4.72 (s, 1H), 4.98 (d, 2H, J=6.24), 6.3 (m, 1H), 7.01 (d, 1H, J=15.48) 7.2–7.6 (c, 15H). Mass spectrum (FAB+, GLY) 479 (M+).

The free acid prodrug is then quantitatively converted to the monosodium salt by combining it with an equal molar amount of sodium bicarbonate in water and stirring at room temperature for 4 hours. The solution is then lyophilized to yield a white solid: $^1$H NMR (D$_2$O, 500 Mhz) δ 3.04 (m, 4H), 3.66 (m, 2H), 3.75 (m, 2H), 4.40 (d, 2H, J=7.55), 4.79 (s, 1H), 5.09 (d, 2H, J=5.9), 6.5–6.6 (c, 1H), 7.23 (d, 1H, J=15.75), 7.5–7.8 (c, 15H). $^{31}$P NMR (D$_2$O, 500 Mhz) δ 2.19 (s). Mass spectrum (FAB+, GLY) 479 (M+).

(3) Synthesis of loxapine prodrug
Materials

Loxapine succinate is obtained from Research Biochemicals Incorporated (Natick, Mass.) Loxapine succinate is converted to the free base prior to reaction.

Methods

Loxapine free base (0.51 mmole) is combined with a five molar excess of 1,2,2,6, pentamethylpiperdidne and a 1.5 molar excess of chloromethyl di-tert-butyl phosphate. The reaction components are solubilized in anhydrous acetonitrile. The reaction is then capped and stirred at 50° C. for 64 hours. The reaction is then placed under reduced pressure to remove the solvent after which time 5 ml of anhydrous ethyl ether is added to precipitate the product. This suspension is then centrifuged and the supernatant is removed. This process is repeated three times. The product is then purified using preparative thin layer chromatography. The eluent is methylene chloride and methanol in a 9 to 1 ratio respectively which gives a Rf of 0.3. The mono tertiary butyl-protected prodrug is isolated as a white solid (0.153 mmole, 25% yield): $^1$H NMR (CD$_3$OD, 300 Mhz) δ 1.46 (s, 9H), 3.24 (s, 3H), 3.51 (m, 2H), 3.78 (m, 4H), 4.05 (m, 2H), 5.05 (d, 2H, J=8.4) 7.00–7.60 (c, 7H). Mass spectrum (FAB+, NBA) 494 (M+).

The protected prodrug (0.153 mmole) is incorporated with 0.81 mmole of triflouroacetic acid in benzene at room temperature for 24 hours to remove the tertiary butyl-protecting groups. The reaction is then placed under reduced pressure to remove TFA and benzene to yield 0.114 mmole (76% yield) of a white solid: $^1$H NMR (D$_2$O, 300 Mhz) δ 3.27 (s, 3H) 3.4–4.2 (c, 8H), 5.08 (d, 2H, J=7.23), 7.10–7.45 (c, 7H). $^{31}$P NMR (D$_2$O, 500 Mhz) δ -1.77 (s). Mass spectrum (FAB+, TG) 438 (M+). $^{13}$C.

(4) Synthesis of amiodarone prodrug
Materials

Amiodarone hydrochloride is obtained from Sigma Chemical Company (St. Louis, Mo.). The hydrochloride is converted to the free base prior to reaction.

Methods

Amiodarone free base (0.417 mmole) is combined with a 2 molar excess of chloromethyl di-tert-butyl phosphate along with a two molar excess of 1,2,2,6,6 pentamethylpiperdidne in 3ml of anhydrous acetonitrile. Sodium iodide (5 mg) is added as a catalyst. The reaction is stirred at 40° C. for 24 hours with protection from light. The reaction is then placed under reduced pressure to remove the solvent at which time 5 ml of anhydrous ethyl ether is added to precipitate the product. This suspension is then centrifuged and the supernatant is removed. This process is repeated three times. The fully tertiary butylated protected prodrug is obtained as a white solid (0.199 mmole, 48% yield): $^1$H NMR (CDCl$_3$, 300 Mhz) δ 0.92 (t, 3H, J=7.32), 1.3–1.85 (c, 28H), 2.89 (t, 2H, J=7.71), 3.88 (q, 4H, J=4.38), 4.4–4.6 (c, 4H), 5.47 (d, 2H, J=7.41) 7.3 (m, 2H), 7.49 (d, 2H, J=8.15), 8.21 (s, 2H). $^{31}$P NMR (CDCl$_3$, 500 Mhz) δ -12.34 (t, J=17.2). Mass spectrum (FAB+, NBA) 868 (M+).

The protected prodrug (0.17 mmole) is incorporated with 0.81 mmole of triflouroacetic acid in benzene at room temperature for 24 hours to remove the tertiary butyl-protecting groups. The reaction is then placed under reduced pressure co remove TFA and benzene to yield a yellow oil which is dissolved in water containing a two molar excess of sodium bicarbonate to create the sodium salt. The aqueous solution is then lyophilized to remove solvent to yield (0.197 mmole) of a white hygroscopic solid (quantitative yield): $^1$H NMR (DMSO, 300 Mhz) δ 0.836 (t, 3H, J=7.23), 0.976 (,m, 2H), 1.31 (m, 6H) 1.68 (m, 2H) 2.74 (m, 2H) 3.54 (m, 4H) 3.84 (m, 2H), 4.36 (m, 2H), 4.95 (d, 2H, J=8.7), 7.22–7.65 (c, 4H), 8.18 (s, 2H). $^{31}$P NMR (D$_2$O, 500 Mhz) δ 4.77 (s). Mass spectrum (FAB+, NBA) 756 (M+).

Example 3
pKa Determination of Quinuclidine Prodrug (1) Quinuclidine prodrug pKa determination by potentiometric titration method A 0.01 M quinuclidine prodrug aqueous solution is titrated using a burette containing a 0.1 N sodium hydroxide volumetric standard solution obtained from Aldrich Chemical Company (Milwaukee, Wis.). The pH is recorded with a calibrated Corning pH/ion analyzer (Corning Incorporated, Corning, N.Y.) after each 0.25 ml addition of NaOH. This experiment is conducted at 25° C.

(2) Quinuclidine prodrug pKa determination by $^{31}$P NMR method

A 0.25 mmole quantity of the loxapine prodrug is dissolved in a 10% v/v D$_2$O in H$_2$O solvent to prepare a stock solution of 10 ml total volume. Samples spanning the expected pKa are made by adding minute volumes of a 0.1 N NaOH aqueous solution and recording the pH with a calibrated Corning pH/ion analyzer (Corning Incorporated, Corning, N.Y.). One half milliliter samples are withdrawn from the stock solution after each pH measurement and transferred to conventional NMR tubes, capped and frozen until analysis at 25° C. Spectra are recorded from a Bruker AM 500 mHz NMR spectrophotmeter which is tuned to the $^{31}$P nucleus. The change in chemical shift is recorded as a function of pH. An insert tube, containing 30% H$_3$PO$_4$, is inserted into each sample NMR tube prior to analysis to serve as an internal reference for the prodrugs' $^{31}$P chemical shift.

(3) Data analysis

The equilibrium for the second ionization of the prodrugs' phosphate monoester is represented by equation (1).

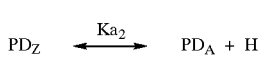

(1)

$PD_Z and PD_a$ represent the prodrug in its zwitterionic and net anionic states respectively (see scheme 6). $Ka_2$ represents the second ionization constant and H represents hydrogen ion. The fraction of prodrug in the zwitterionic form (fz) and the fraction in the net anionic form (fa) are expressed in equations (2) and (3) respectively.

$$f_z = \frac{H}{H + Ka} \quad (2)$$

$$f_A = \frac{Ka}{H + Ka} \quad (3)$$

The observed chemical shift ($\delta_{obs}$) of the $^{31}P$ signal is expressed in equation (4).

$$\delta_{obs} = f_Z \times \delta_Z + f_A \times \delta_A \quad (4)$$

Where $\delta_z$ and $\delta_a$ represents the chemical shift for the zwitterionic and net anionic prodrug respectively. Substituting equations (2) and (3) into equation (4) gives equation (5).

$$\delta_{obs} = \frac{H \times \delta_z + Ka \times \delta_A}{H + Ka} \quad (5)$$

Sigma Plot 4.14 (Jandel Scientific) was used to curve fit the experimental results to equation (5).

(4) Results

The loxapine prodrug, as well as all the described prodrugs, will have the following ionization scheme shown in Reaction V, where (1) is the net cationically charge form, (2) is the zwitterionic or neutral form, and (3) is the net anionically charged form. $Ka_1$ and $Ka_2$ are the ionization constants.

(Reaction V)

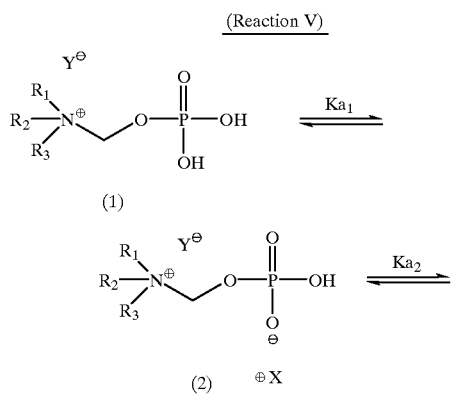

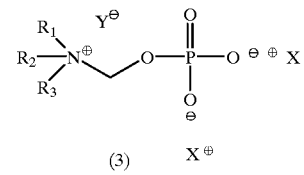

The first ionization constant, $Ka_1$, is expected to be low and to be of little physiological importance; however, $Ka_2$ is of much greater importance. With this in mind, the second ionization constant ($Ka_2$) for the phosphate monoester promoiety of the quinuclidine was determined by two methods. These methods were potentiometric titration and $^{31}P$ NMR. The potentiometric titration is by far the most traditional and accepted means for estimating pKa values; however, it has one main disadvantage. It requires significant quantities of, difficult to synthesize, prodrug. The quinuclidine prodrug is, by far, the simplest prodrug to synthesize and was chosen for the following experiments for that reason. For the potentiometric titration method, the volume of base added was plotted against the change in pH. This plot allows one to determine the volume of base required to reach the endpoint of the titration. The pH at the point where the volume of base added is equal to one half that required to reach the endpoint is, by definition, the point where pH is equal to pKa (Albert, A., and Serjeart, E., 1984) The pKa determined by potentiometric titration was found to be 5.0 and the pKa determined bag $^3P$ NMR was found to be 4.9.

Example 4

Loxapine Prodrug pKa Determination (1) $^{31}P$ NMR method

A 0.25 mmole quantity of the loxapine prodruct is dissolved in a 10% v/v $D_2O$ in $H_2O$ solvent to prepare a stock solution of 10 ml total volume. Samples spanning the expected pKa are made by adding minute volumes of a 0.1 N NaOH aqueous solution and recording the pH with a calibrated Corning pH/ion analyzer (Corning Incorporated, Corning, N.Y.). One half milliliter samples are withdrawn from the stock solution after each pH measurement and transferred to conventional NMR tubes, capped and frozen until analysis at 25° C. Spectra are recorded from a Varian XL 300 mHz NMR spectrophotometer which is tuned to the $^{31}P$ nucleus. The change in chemical shift is recorded as a function of pH. An insert tube, containing 30% $H_3PO_4$, is inserted into each sample NMR tube prior to analysis to serve as an internal reference for the prodrugs' $^{31}P$ chemical shift.

(2) Data analysis

The data analysis for the loxapine prodrugs $^3P$ NMR pKa determination is the same as that reported for the quinuclidine prodrug in Example 3.

(3) Results

The pKa was found to be 4.7.

Example 5

Solubility Improvements (1) Loxapine free base solubility

The solubility behavior of loxapine is studied as a function of pH. Loxamine succinate is obtained from Research Biochemicals Incorporated (Natick, Mass.). Loxapine succinate is converted to the free base before conducting experiments. Each pH solution is a 0.05 M buffered solution with an ionic strength adjusted to $\mu=0.2$ with NaCl. The pH values along with their buffer composition are listed: pH 3.24, HCl/CH$_3$COONa; pH 3.96 and 4.96, CH$_3$COOH/CH$_3$COONa; pH 5.82–7.94, NaH$_2$PO$_4$/Na$_2$HPO$_4$; pH 8.95 and 9.98, H$_3$BO$_3$/NaOH. The volume of buffer used in the experiments varies; samples with pH equal to or below 4.96 utilize 2 ml of buffer whereas the higher pH samples has a volume of 5 ml. To vials containing the volume of buffer are added excess of loxapine free base. The vials are then capped, sonicated and vortexed prior to submersion in a constant temperature shaking water bath at 25° C. The samples are shaken at a rate of 100 shakes/min. for at least 24 hours. Afterwards the excess solid drug is removed from the saturated solution either by centrifugation (samples with pH greater than 5) or by filtration through a 0.45 μm Acrodisc membrane filter (Gelman). The filtrates/supernatants are then appropriately diluted for quantification by HPLC. The HPLC conditions for the quantification of loxapine are as follows: Reversed-phase HPLC is carried out using a Shimadzu 6A-HPLC pump (Shimadzu Corp., Kyoto, Japan), a Shimadzu SPD-6A UV spectrophotometer (Shimadzu Corp.), a Shimadzu CR601 integrator (Shimadzu Corp.) and a Rheodyne injector (Rheodyne, Berkeley, Calif.) fitted with a 20 μl injection loop. A C-18 reversed phase column (150×4 mm, ODS Hypersil, 5 μm particle size) is used for the analysis. The HPLC assays are carried out using UV detection at 254 nm. The mobile phase consists of acetonitrile and 25 mM of aqueous potassium phosphate monobasic solution adjusted to pH 3.8 with phosphoric acid. 0.15% of triethylamine is contained in the aqueous buffer. The ratio of organic:aqueous is 25:75 for analysis of loxapine prodrug and 60:40 for analysis of loxapine free base. The retention times are 5 min. and 7 min. for loxapine prodrug and loxapine free base respectively, when the flow rate is adjusted to 1 ml/min.

(2) Loxapine prodrug solubility

Each pH solution contains 0.05 M buffer with an ionic strength adjusted to μ=0.2 with NaCl. The pH 3 buffer composition is HCl/CH$_3$COONa; whereas, the pH 7.4 buffer composition is NaH$_2$PO$_4$/Na$_2$HPO$_4$. The volume of buffer used in the experiments is 150 μl. To this is added excess of the loxapine prodrug in one ml glass screw top vials. The vials are then capped, sonicated and vortexed prior to submersion in a constant temperature shaking water bath at 25° C. The samples are shaken at a rate of 100 shakes/min. for at least 24 hours. The suspensions are then placed in a micro centrifuge to precipitate the excess drug. A volume of 50 μl of the supernatant is then appropriately diluted with water for quantification by reverse phase HPLC. The HPLC conditions for the quantification of loxapine are as follows: Reversed-phase HPLC is carried out using a Shimadzu LC-10AT pump (Shimadzu Corp., Kyoto, Japan), a Shimadzu SPD-10A UV spectrophotometer (Shimadzu Corp.), a Shimadzu SCL-10A system controller, a SIL-10A auto injector, a Rheodyne injector (Rheodyne, Berkeley, Calif.) fitted with a 50 μl injection loop and the software for the integration is Class VP Chromatography Data System, Version 4.1 (Shimadzu Corp.). A C-18 reversed phase column (150×4 mm, ODS Hypersil, 5 μm particle size) is used for the analysis. The HPLC assays are carried out using UV detection at 254 nm. The mobile phase consists of acetonitrile and 25 mM of aqueous potassium phosphate monobasic solution adjusted to pH 3.8 with phosphoric acid. 0.15% of triethylamine is contained in the aqueous buffer. The ratio of organic:aqueous is 32:68. The retention time is 4.2 min. when the flow rate is adjusted to 1 ml/min.

(3) Results and discussion

Figure 2:
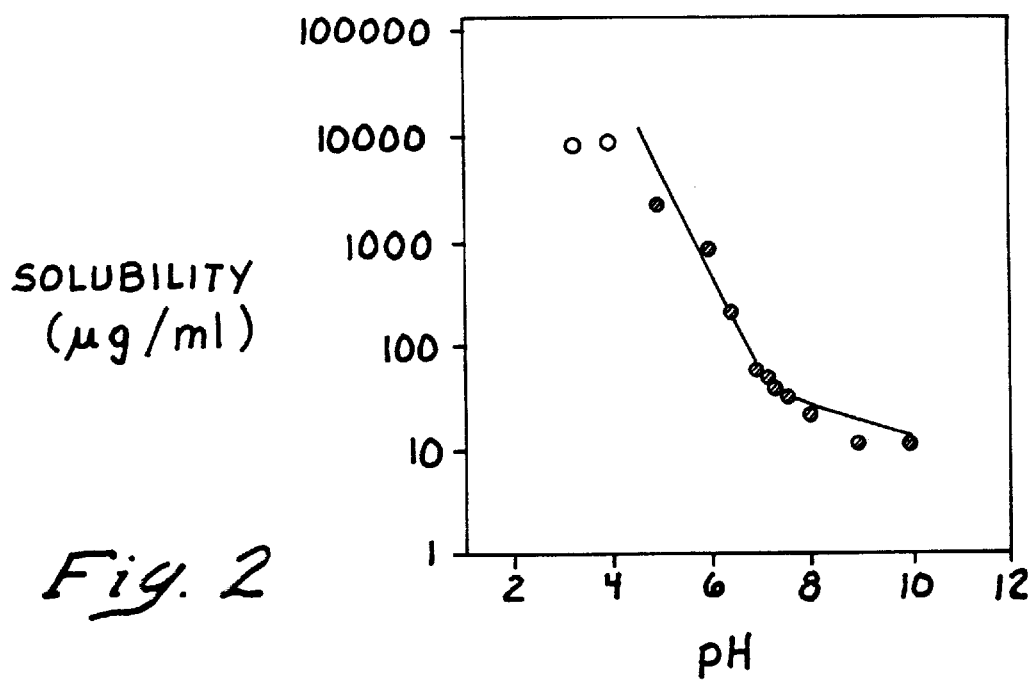
FIG. 2 shows the pH solubility profile for loxapine.

In order for the novel prodrug approach to have clinical usefulness, the prodrug must have adequate water solubility in the physiologically acceptable pH range. In an effort to demonstrate the enhancement in solubility through the described prodrug approach, the following section will compare the solubility behavior of loxapine free base to that of the loxapine prodrug. Loxapine free base has an intrinsic solubility which was experimentally determined to be 12.6 μg/ml. The pH-solubility profile for loxapine is shown in FIG. 2. The solid points represent the experimentally determined solubilities. The solid line is the theoretical plot of the solubility profile obtained through curve fitting. The open circles represent the intrinsic solubility of the loxapine salt.

The solubility rises upon lowering of the pH. This behavior is typical for basic drugs if no other acidic or basic functionalities exist on the molecule. The solubility will begin to increase with lowering pH and will continue to increase until the intrinsic solubility of the salt of the tertiary amine is attained. The solubility behavior is a function of the pKa of the basic functional group. With this pH solubility profile, the pKa was calculated, through a curve fitting procedure, and was found to be 7.52. The currently available parenteral IM injection of loxapine is available as loxapine hydrochloride with polysorbate 80 (5% w/v) and propylene glycol (70% v/v) [22]. The polysorbate 80 and propylene glycol are used as cosolvents in order to attain a concentration equivalent to 50 mg/ml of loxapine. The need for the cosolvents is evident from FIG. 2 because even at pH of 3.24 the solubility is only 8.23 mg/ml.

The prodrugs pKa is also an important constant, especially evaluating the solubility behavior. At several pH units below the pKa (e.g. pH 3), the prodrug should predominately exist in its least soluble form which is the zwitterionic form. At several pH units above the pKa (e.g. pH 7.4), the prodrug should exist predominantly in its most water soluble form which is the form with a net anionic charge (the net cationic form of the prodrug is physiologically unimportant and is not considered here). The solubility of the loxapine prodrug was then measured at pH 3 and 7.4 to obtain an estimate of the solubility profile of the prodrug in the physiological relevant pH range. The experimentally determined loxapine prodrug aqueous solubilities at two pH values are listed in Table 1.

TABLE 1

| pH | Solubility (mg/ml) |
|---|---|
| 3.0 | 290.5 ± 2.9 |
| 7.4 | 648.2 ± 0.6 |

Figure 3:
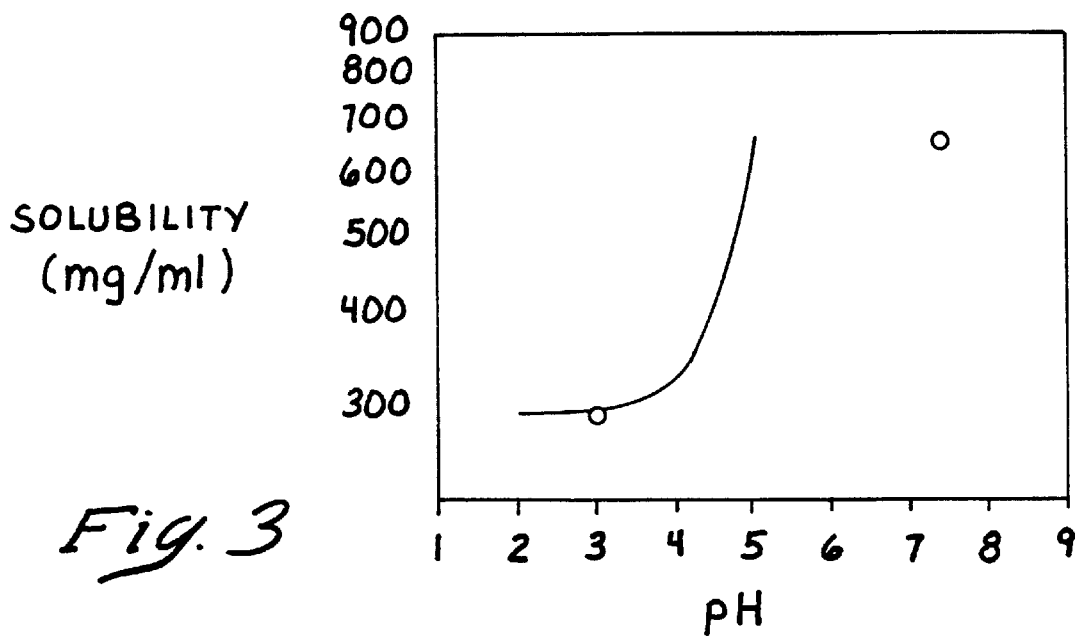
FIG. 3 shows a theoretical solubility profile for loxapine prodrug.

The solubilities were found to be 290.5±2.9 and 648.2±0.6 mg/ml at pH values 3.0 and 7.4 respectively. The loxapine prodrug offers a 15,843 fold increase in loxapine solubility compared to the free base. This translates to solubility limits which are 9.7 times on that which are used in the parenteral formulation without the need of the aforementioned cosolvents. Using these values along with the pKa a theoretical pH-solubility profile is illustrated in FIG. 3.

The open circles are the experimentally determined solubilities at their respective pH values. The line represents the theoretical solubility profile for a weak acid. The equation for this plot is $$\log S_t = \log\left[\frac{H}{K_2} + 1\right] + \log S_o$$

$S_t$ is the total solubility, H is the hydrogen ion molar concentration, $K_2$ is the second ionization constant for the prodrugs phosphate monoester functionality, and $S_o$ is the intrinsic solubility of the weak acid. In construction this line the prodrug solubility at pH 3.0 was used for the $S_o$. This value for So is only an approximation of the minimum solubility based upon the determined pKa.

(4) Solubility estimates of synthesized prodrugs

The present prodrugs are designed to increase the aqueous solubility and safety of amine-containing drugs. Preliminary visual solubility estimates for each of the prodrugs are listed below in Table 2.

TABLE 2

| Prodrug Name | pH 7.4 solubility estimate (mg/ml) |
|---|---|
| cinnarizine | >5 |
| loxapine | >600 |
| amiodarone | >5 |

Example 6
Enzymatic Liability Assessment of Selected Prodrugs (1) Preparation of i.v. injections Cinnarizine for i.v. injection was prepared in a 10 mM phosphate buffer solution at pH 4.5 at a concentration of 12.5 mg/10 ml (3.39 mM) along with 37.5 mM sulfobutylether 4 beta-cyclodextrin as a solubilizing excipient. The cyclodextrin solution (10 ml) was prepared first and the pH adjusted to 3.5 with HCl. The cinnarizine was then added and the solution was sonicated for three hours and subsequently stirred overnight. The pH was then adjusted to 4.5 with NaOH along with the addition of 29 mg of NaCl to adjust for isotonicity. The solution was then passed through a 0.22 μM nylon-membrane filter just prior to administration. The prodrug injection was prepared by dissolving 16.97 mg or cinnarizine prodrug in 10 ml of 0.9% NaCl sterile solution (3.39 mM) for injection. The solution was passed through a 0.22 μM nylon-membrane filter just prior to injection.

(2) Pharmacokinetic evaluation

The evaluation of the cinnarizine plasma concentration versus time was conducted with a male beagle dog weighing 11.1 kg. The dog received the cinnarizine injection followed by a two-week washout period then received the prodrug injection in an equal molar quantity. Samples were taken from the dog prior to dosing (10 ml blank plasma) and 2, 6, 10, 20, 40 min and 1, 2, 4, 6, 8, 24 hours post-dosing (3 ml each). Blood samples were drawn from either cephalic, saphenous, or jugular vein. The samples were centrifuged for 10 minutes and 1 ml of plasma was measured and frozen at −20° C. prior to sampling by HPLC. The dog received a regular diet between experiments and was fasted the day of the experiment.

(3) Analytical procedure

Plasma concentrations of cinnarizine were determined by HPLC with fluorescence detection. To each one milliliter of plasma was added: 100 μL of acetonitrile-H2O (70:30, v/v), containing 40 μg meclizine (internal standard), and 100 μL of 0.5 M HCl. The plasma sample was then vortexed for 30 seconds. One ml of carbon tetrachloride was then combined with the sample for an additional one minute of vortexing. Samples were then centrifuged for ten minutes after which the carbon tetrachloride was removed and evaporated to dryness under a stream of dry nitrogen. The residue was then redissolved in 200 μL of acetonitrile-H2O (70:30, v/v) prior to sampling by HPLC. The results were calculated from peak area ratios. A six-point standard curve was obtained using the above procedure with addition of cinnarizine concentrations in the range of 5.5 to 550 ng/ml of plasma. A three-point calibration was performed on the day of the study using high, medium and low cinnarizine concentrations. This calibration was used for the quantification of cinnarizine concentration in the samples.

The HPLC system consisted of a Shimadzu LC-6A pump (Kyoto, Japan), a Rheodyne 7125 injector (Cotati, Calif.), a Shimadzu RF-535 Fluorescence HPLC monitor (Kyoto, Japan), and a Shimadzu CR-601 integrator (Kyoto, Japan). The HPLC conditions were as follows: injection volume, 50 μL; flow rate, 1.5 ml/min; excitation at 260 nm and emission at 315 nm. The stationary phase was a C18 ODS Hypersil reverse phase column (15 cm×4.6 mm i.d., 5 μM). The mobile phase was a 7 to 3 ratio of aceronitrile to buffer, respectively. The buffer consisted of 25 mmole potassium dihydrogen phosphate (adjusted to pH 3.9 with phosphoric acid) and 10 mM tetrabutyl ammonium dihydrogen phosphate. Under these conditions the retention times for cinnarizine and meclizine were 14.5 and 17.7 min respectively.

(4) Data analysis

Pharmacokinetic analysis was performed on the semilogarithmic plot of cinnarizine plasma concentration versus time post dosing for both the cinnarizine and cinnarizine prodrug injections. In both cases the disappearance of cinnarizine could be described by a triexponential equation fitted using Sigma Plot 4.14 (Jandel Scientific). The equation had the form: $C = A_{1e}^{-A1t} + A_{2e}^{-A2t} + A_{3e}^{-A3t}$, where t is time. Plasma terminal half life ($t_{1/2}$) is calculated from $t_{1/2}=0.693/\lambda_3$. Areas under the concentration versus time curves from zero to infinity ($AUC_{0-\infty}$) following the iv injection were estimated by using the equation $AUC_{0-\infty}=A_1/\lambda_1+A_2/\lambda_2+A_3/\lambda_3$. Clearance values (Cl) were calculated from $Cl=D/AUC_{0-\infty}$, where D is the iv dose. The volume of distribution (V) was calculated from $V=D/(\lambda_3 \times AUC_{0-\infty})$.

(5) Results

Figure 5:
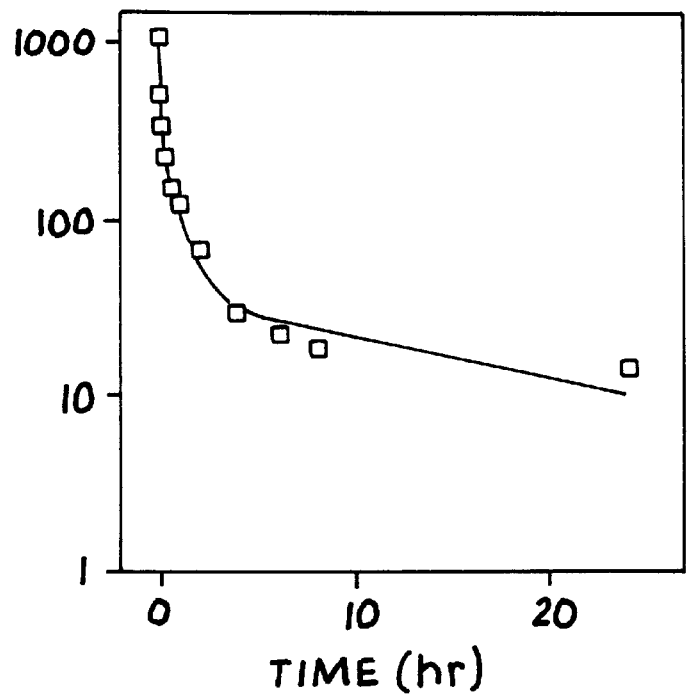
FIG. 5 shows the semilogarithmic plot of cinnarizine concentration in plasma versus time after i.v. injection of 33.9 nmole of cinnarizine prodrug to the beagle dog.

Both cinnarizine and the cinnarizine prodrug injections caused no observable signs of discomfort or toxicity to the dog. The semilogarithmic clots of cinnarizine concentration (ng/ml) versus time (h) are shown in FIGS. 4 and 5 for the cinnarizine and cinnarizine prodrug injections respectively. FIG. 4 presents the semilogarithmic clot of cinnarizine concentration in plasma versus time after iv injection of 33.9 nmole of cinnarizine to the beagle dog.

FIG. 5 presents the semilogarithmic plot of cinnarizine concentration in plasma versus time after iv injection of 33.9 nmole of cinnarizine prodrug to the beagle dog.

The triexponential equations obtained from the computer curve for the cinnarizine and cinnarizine prodrug inflections are $C=469.0e^{-14.80t}+198.5e^{-1.03t}+38.53e^{-0.057t}$, and $C=1476.0e^{-18.67t}+289.2e^{-1.24t}+35.9e^{-0.055t}$, respectively. Table 3 shows a comparison of the various pharmacokinetic parameters calculated.

TABLE 3

|  | $AUC_{0-\infty(ngh/ml)}$ | $t_{1/2}$ (h) | Cl (L/h/kg) | Vd (L/kg) |
|---|---|---|---|---|
| Cinnarizine | 900.8 | 12.0 | 1.17 | 21.7 |
| Cinnarizine prodrug | 964.1 | 12.6 | 1.17 | 21.2 |

From analysis of FIGS. 4 and 5 along with Table 1 can be reasoned that the cinnarizine prodrug has rapidly and quantitatively converted to cinnarizine upon intravenous administration to the dog.

References

Albert, A., Serjeant, E. P., *The Determination of Ionization Contants. A Laboratory Manual*. New York, Chapman and Hall, 1984.

American Hospital Formulary Service, *Drug Information*, Brethesda, American Society of Hospital Pharmacists, 1993.

Bodor, N. S., Labile, non-heterocyclic quaternary ammonium salt/esters as transient derivatives. U.S. Pat. No. 4,160,099, Jul. 3, 1979.

Bodor, N. S. and L. A. Freiberg, Salts of erythromycin A esters. U.S. Pat. No. 4,264,765, Apr. 28, 1981.

Bodor, N. S., Selected quaternary ammonium salts of pilocarpine useful in reducing intraocular pressure in warm-blooded animals. U.S. Pat. No. 4,061,722, Dec. 6, 1977.

Bodor, N., Novel approaches in prodrug design. Drugs of the Future, 1981. VI(3): p. 165–182.

(a) Bodor, N., J. J. Kaminski, and S. Selk, Soft drugs. 1. Labile quaternary ammonium salts as soft antimicrobials. J. Med. Chem., 1980. 23(5): p. 469–474.

Bodor, N., The soft drug approach. Chem. Tech., 1984. 14: p. 28–38.

(b) Bodor, N., Woods, R., Raper, C., Kearney, P., Kaminski, J. J., Soft drugs. 3. A new class of anticholinergic agents. J. Med. Chem., 1980. 23(5): p. 474–480.

Bodor, N. and J. J. Kaminski, Soft drugs. 2. Soft alkylating compounds as potential antitumor agents. J. Med. Chem., 1980. 23(5): p. 566–569.

Bodor, N., Novel approaches for the design of membrane transport properties of drugs, in Design of biopharmaceutical properties through prodrugs and analogs, E. B. Roche, Editor. 1977, Academy of pharmaceutical sciences: Washington. p. 98–135.

Bogardus, J. B. and T. Higuchi, Kinetics an mechanism of hydrolysis of labile quaternary ammonium derivatives of tertiary amines. J. Pharm. Sci., 1982. 71(7): p. 153–159.

Davidson, S. K., et al., N-(Acyloxyalkyl)pyridinium salts as soluble prodrugs of a potent platelet activating factor antagonist. J. Med. Chem., 1994. 37(26): p. 4423–4429.

Golik, J., et al., Phosphonooxymethyl ethers of taxane derivatives. European Patent 0 604 910 A1, Dec. 23, 1993.

Hammer, R. H., Gunes, E., Kumar, G. N., Wu, W. M., Srinivasan, V. and Bodor, N. S., Soft drugs—XIV. Synthesis and anticholinergic activity of soft phenylsuccinic analogs of methatropine. Bioorganic & Medicinal Chemistry, 1993. 1(3): p. 183–187.

Tercel, M., W. R. Wilson, and W. A. Denny, Nitrobenzyl mustard quaternary salts: A new class of hypoxia-selective selective cytotoxins showing very high in vitro selectivity. J. Med. Chem., 1993. 36(17): p. 2578–2579.

(a) Varia, S. A., Schuller, S., Sloan, K. B., Stella, V. J. Phenytoin prodrugs III. Water-soluble prodrugs for oral and/or partenteral use. Journal of Pharmaceutical Sciences, 1984. 73(8): p. 1068–1073.

(b) Varia, S. A., Schuller S., and Stella, V. J. Phenytion Prodrugs IV: Hydrolysis of Various 3-(Hydroxymethyl) phenytion Esters. Journal of Pharmaceutical Sciences, 1984. 73(8): p. 1074–1079.

(c) Varia, S. A., Stella, V. J., Phenytlon prodrugs V: In Vivo Evaluation of Some Water-Soluble Phenytion Prodrugs in Dogs. Journal of Pharmaceutical Sciences, 1984. 73(8): p. 1080–1086.

(d) Varia, S. A., Stella V. J., Phenytion Prodrugs VI: In Vivo Evaluation of a Phosphate Ester Prodrug of Phenytoin after Parenteral Administration to Rats. Journal of Pharmaceutical Sciences, 1984. 738): p. 1087–1090.

Vinogradova, N. D., S. G. Kuznetsov, and S. M. Chigareva, Quaternary ammonium salts with labile N+-C bonds as drug precursors. Khim.-Farm. Zh., 1980. 14: p. 41–47.

Zwierzak, A. and M. Kluba, Organophosphorus ester—I t-butyl as protecting group in phosphorylation via nucleo-phillic displacement. Tetrahedron, 1971. 27: p. 3163–3170.

We claim:

1. N-phosphoryloxymethyl prodrugs of tertiary amine containing drugs having the following formula VIa or VIb,

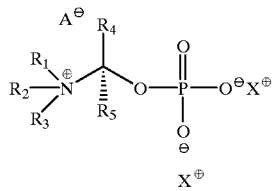

(Formula VIa)

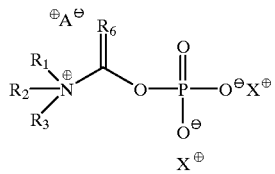

(Formula VIb)

wherein $R_1$, $R_2$ and $R_3$ are substituents which comprise the parent tertiary amine, $R_4$ and $R_5$ are each hydrogen or an organic residue selected from the group consisting of a straight-chain, substituted or unsubstituted aliphatic group, a substituted or unsubstituted aromatic group, and a substituted or unsubstituted cyclic group, $R_4$ and $R_5$ may contain one or more heteroatoms and may also be joined to form a ring, $R_6$ is a group double bonded to the carbon spacer, which is an organic residue as defined for $R_4$ and $R_5$, and X is an organic or inorganic cation, and A represents an anion.

2. The prodrug of claim 1 wherein $R_4$ and $R_5$ are each selected from the group consisting of $-CH_3$, $-C_2CH_3$, phenyl, benzyl, and cyclohexane.

3. The prodrug of claim 1 wherein X is selected from the group consisting of sodium, potassium, ammonium and other pharmaceutically acceptable cations.

4. The prodrug of claim 1 wherein the aqueous solubility of the compound is at least 5 mg/ml.

5. A composition containing an N-phosphoryloxymethyl prodrug of tertiary amine containing drugs having the following formula VI,

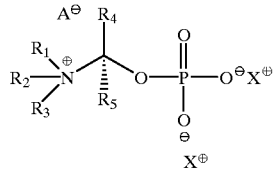

(Formula VI)

wherein $R_1$, $R_2$ and $R_3$ are substituents which comprise the parent tertiary amine, $R_4$ and $R_5$ are each hydrogen or an organic residue selected from the group consisting of a straight-chain, substituted or unsubstituted aliphatic group, a substituted or unsubstituted aromatic group, and a substituted or unsubstituted cyclic group, $R_4$ and $R_5$ may contain one or more heteroatoms and may also be joined to form a ring, and X is an organic or inorganic cation, A represents an anion, and a pharmaceutically acceptable carrier thereof.

6. The composition of claim 5 wherein the pharmaceutically acceptable carrier is aqueous.

7. The composition of claim 5 wherein the pH of the composition is a physiological acceptable pH range.

8. The composition of claim 5 for intravenous, oral or parenteral administration.

9. The composition of claim 5 wherein the composition is lyophilized.

10. A method of making a soluble prodrug of a tertiary amine containing parent drug comprising derivatization of a prodrug moiety of formula VII (Formula VII)

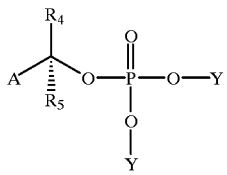

wherein A represents a leaving group, $R_4$ and $R_5$ are each hydrogen or an organic residue selected from the group consisting of a straight-chain, substituted or unsubstituted aliphatic group, a substituted or unsubstituted aromatic group, and a substituted or unsubstituted cyclic group, $R_4$ and $R_5$ may contain one or more heteroatoms and may also be joined to form a ring, and Y is a phosphate protecting group,
through the nucleophilic attack of a tertiary amine causing the displacement of A, followed by the removal of the protecting groups.

11. The method of claim 10 wherein A is selected from the group consisting of chlorine, bromine, iodine, tosylate, florine, acetate, hydroxyl and triflate.

12. The method of claim 10 herein Y is a phosphate protecting groups that temporarily blocks the reactive phosphate moiety and permits selective displacement with the nucleophilic deplacement reaction.

13. The method of claim 10 wherein Y is selected from the group consisting of benzyl, tertiary butyl and isopropyl, ethyl and β-cyanoethyl.

14. A method of making a soluble prodrug of a tertiary amine containing parent drug comprising reaction of a compound of the following Formula VIII (Formula VIII)

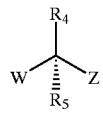

wherein $R_4$ and $R_5$ are each an organic or inorganic residue, and W and Z are leaving groups, with a tertiary amine to displace one of either W or Z and reacting the remaining leaving group with a protected phosphate.

15. The method of claim 14 wherein the W and Z are each independently selected from the group consisting of chlorine, bromine, iodine, tosylate, fluorine, acetate, hydroxyl and triflate.

* * * * *